United States Patent [19]

Nojima

[11] Patent Number: 5,681,551
[45] Date of Patent: Oct. 28, 1997

[54] OIL-BASED SOLID COSMETIC COMPOSITION

[75] Inventor: Kazuhiko Nojima, Chiba, Japan

[73] Assignee: Kao Corporation, Tokyo, Japan

[21] Appl. No.: 357,064

[22] Filed: Dec. 14, 1994

Related U.S. Application Data

[63] Continuation of Ser. No. 997,524, Dec. 28, 1992, abandoned.

[30] Foreign Application Priority Data

Dec. 26, 1991 [JP] Japan ................................. 3-345107

[51] Int. Cl.$^6$ ........................................................ A61K 7/027
[52] U.S. Cl. ................................ 424/64; 424/61; 424/63; 424/DIG. 5
[58] Field of Search .................................. 424/401, 61, 63, 424/64, DIG. 5

[56] References Cited

U.S. PATENT DOCUMENTS

| | | | |
|---|---|---|---|
| 3,641,239 | 2/1972 | Mohrlok | 424/64 |
| 5,015,469 | 5/1991 | Yoneyama et al. | 424/59 |
| 5,176,902 | 1/1993 | Castro et al. | 424/63 |
| 5,210,251 | 5/1993 | Ohashi et al. | |
| 5,266,321 | 11/1993 | Shukuzaki et al. | 424/401 |
| 5,470,563 | 11/1995 | Tanaka et al. | 424/448 |

FOREIGN PATENT DOCUMENTS

| | | |
|---|---|---|
| 0 266 921 A2 | 5/1988 | European Pat. Off. |
| 0266921 | 5/1988 | European Pat. Off. |
| 0 331 833 | 9/1989 | European Pat. Off. |
| 0374332 | 6/1990 | European Pat. Off. |
| 61-66752 | 4/1986 | Japan |
| 1-96111 | 4/1989 | Japan |
| 01-143812 A | 9/1989 | Japan |
| 01143812 | 9/1989 | Japan |
| 0288513 | 6/1990 | Japan |

OTHER PUBLICATIONS

Kirk-Othmer Encyclopedia of Chemical Technology, 3rd Edition, Published by John Wiley & Sons, 1979, vol. 7, pp. 143,145, 165 and 166.
Patent Abstracts of Japan, vol. 14, No. 284 (C-730) (4227), Jun. 20, 1990, JP-A 2 88 513, Mar. 28, 1990.
Patent Abstracts of Japan, vol. 13, No. 399 (C-632) (3747), Sep. 5, 1989, JP-A-11 43 812, Jun. 6, 1989.
Patent Abstracts Of Japan, vol. 11, No. 60 (C-405) (2507), Feb. 24, 1987, JP-A-61 218 509, Sep. 29, 1986.
Patent Abstracts Of Japan, vol. 12, No. 82 (C-481) (2929), Mar. 15, 1988, JP-A-62 216 635, Sep. 24, 1987.
Patent Abstracts Of Japan, vol. 11, No. 133 (C-418) (2580), Apr. 25, 1987, JP-A-61 271 030, Dec. 1, 1986.
Patent Abstracts of Japan, vol. 9, No. 283 (C-313) (2006), Nov. 9, 1985, JP-A-60 126 209, Jul. 5, 1985.

Primary Examiner—John C. Bleutge
Assistant Examiner—Robert H. Harrison
Attorney, Agent, or Firm—Oblon, Spivak, McClelland, Maier & Neustadt, P.C.

[57] ABSTRACT

An oil-based solid cosmetic composition comprising one or more polyoxyalkylene modified silicones and one or more conventional cosmetically acceptable oils, pigments, paints or a mixture thereof, is provided to give a cosmetic having excellent feel during use and prolonged beautiful make-up appearance.

12 Claims, No Drawings

5,681,551

OIL-BASED SOLID COSMETIC COMPOSITION

This application is a continuation of application Ser. No. 07/997,524, filed on Dec. 28, 1992, now abandoned.

BACKGROUND OF THE INVENTION

1. Field of the Invention

The present invention relates to an oil-based solid cosmetic composition which provides excellent feel upon use, and beautiful make-up appearance for a prolonged period of time.

2. Description of the Background Art

Conventional oil-based make-up cosmetic compositions, such as lipsticks, eye shadows, eye liners and oil-base foundations have disadvantages such as having a tendency to run or ooze, causing spots on clothing, and deterioration of the fresh make-up's appearance in a short period of time.

Several approaches to solving these problems have been proposed. Incorporation of a volatile oil into the makeup has been suggested so that, after application of the cosmetic composition, the oil evaporates leaving the coloring agents and waxes on the skin surface, thus improving the stay of the cosmetic composition. Use of a film-forming agent such as a polymer agent in combination with a volatile oil has also been suggested to improve the stay of the cosmetic composition by forming a polymer film on the skin surface after the composition is applied to the skin and dried.

However, incorporation of a volatile oil into a cosmetic composition is accompanied by a loss in the gloss of the composition over time, which is especially a problem in the case of lipsticks. Additionally, since the volatile oil evaporates over time, the shape of the lipstick becomes thinner, and the stability over time is poor.

SUMMARY OF THE INVENTION

Accordingly, one object of the present invention is to provide an oil-based solid cosmetic composition which gives excellent feel during use, and prolonged beautiful appearance.

A further object of the present invention is to provide an oil-based solid cosmetic composition which comprises one or more polyoxyalkylene modified organopolysiloxanes.

These and other objects have been satisfied by the discovery of an oil-based solid cosmetic composition comprising one or more polyoxyalkylene modified organopolysiloxanes and cosmetically acceptable pigments or oils or a mixture therof.

DETAILED DESCRIPTION OF THE INVENTION AND PREFERRED EMBODIMENTS

The present invention relates to an oil-based solid cosmetic composition which comprises one or more polyoxyalkylene modified organopolysiloxanes and cosmetically acceptable pigments or oils or a mixture thereof.

The polyoxyalkylene modified organopolysiloxane of the present invention (hereinafter referred to as polyether modified silicones) is a compound represented by one of the following formulas (1) to (4):

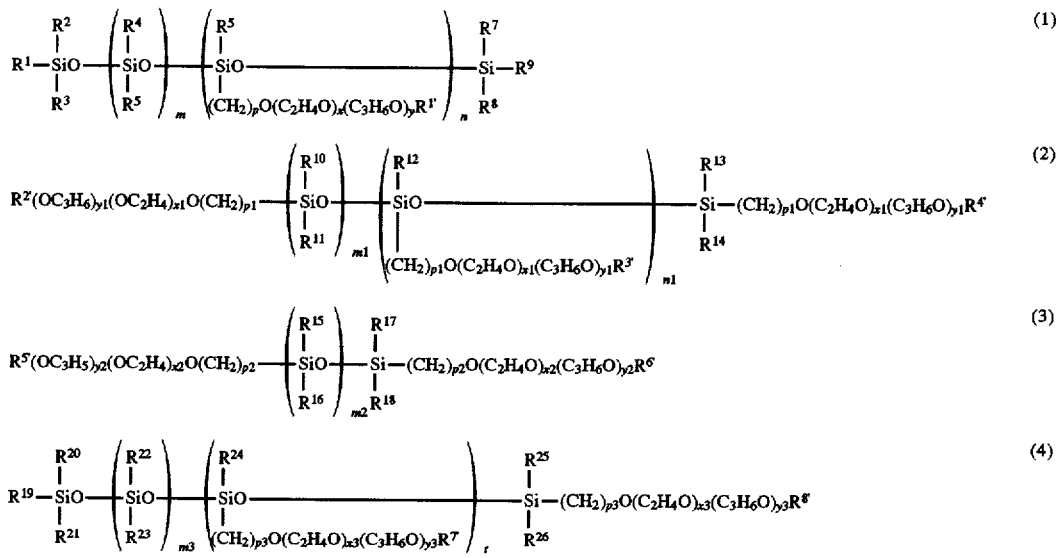

wherein $R^1$ to $R^{26}$ are the same or different from each other, and independently represent $C_1$ to $c_{32}$ linear or branched alkyl, a hydrogen atom or a phenyl group; $R^{1'}$ to $R^{5'}$ are the same or different from each other, and independently represent a $C_1$ to $C_{32}$ linear or branched alkyl group or a hydrogen atom; p, p1, p2 and p3 independently denote a number from 1 to 18; and x, x1, x2, x3, y, y1, y2, y3, m, m1, m2, m3, n, n1 and t are average numbers which make the proportion of the polyoxyalkylene group contained in the molecule from 1 to 50% by weight, preferably from 5 to 40% by weight.

Preferred polyether modified silicones (1) to (4) are those which satisfy the following conditions:

$R^1$ to $R^{26}$: $C_1$ to $C_{25}$ linear or branched alkyl, wherein a portion of them may be a hydrogen atom, $R^{1'}$ to $R^{8'}$: a hydrogen atom or $C_1$ to $C_{18}$ linear or branched alkyl, p to p3: 1 to 20, x to x3: 1 to 50, y to y3: 0 to 50, m to m3: 1 to 500, n to n1: 1 to 100,
t: 1 to 100.
Most preferably the following conditions should be met:
$R^1$ to $R^{25}$: $C_1$ to $C_{22}$ linear or branched alkyl, wherein a portion of them may be a hydrogen atom,
$R^{1'}$ to $R^{8'}$: a hydrogen atom,
p to p3:1 to 5,
x to x3: 1 to 50,
y to y3: 0 to 20,
m to m3: 10 to 300,
n to n1: 1 to 50,
t: 1 to 50.

The polyether modified silicones (1) to (4) are commercially available from Nippon Unicar K. K., Shin-estu Kagaku Kogyo K. K., Toray Dowcorning Silicone E. X. or Toshiba Silicone K. K.

When water is added to an oil-based solid cosmetic composition of the present invention which comprises one or more of the polyether modified silicones (1) to (4) in a weight ratio of water to oil-based solid cosmetic composition of from 1:10 to 1:5, the relative viscosity of the composition increases to a value from 1.1 to 2.0 (relative to the viscosity of the water-free composition as 1). This increase in viscosity is especially favorable with respect to the feel of the makeup during use and prolonged beautiful appearance. The relative viscosity of the composition can be measured with an NR-3 Soliguid meter equipped with a cone plate (cone diameter: 1.798 cm, cone angle: 4.984 deg., Frequency: 1 Hz, 34° C.) manufactured by Rheology K. K.

It is essential that the polyether modified silicone of the present invention contains from 1 to 50% by weight, preferably 5 to 40% by weight, of a polyoxyalkylene group in the molecule in order to achieve excellent feel and prolonged beautiful appearance of the make-up. If the polyoxyalkylene groups are present outside this range, the effects of the invention cannot be obtained.

Further, it is preferred that the polyether modified silicones be contained in the cosmetic composition in an amount from 0.1 to 50%, more preferably from 5 to 30% by weight based on the total weight of the composition. Amounts less than 0.1% by weight will not provide a sufficient lifetime of make-up appearance, while amounts exceeding 50% by weight allow the feel of the make-up to deteriorate rapidly during use.

It is preferred that the oil-based solid cosmetic compositions according to the present invention contain one or more of the above described polyether modified silicones, oil ingredients and pigments but be substantially free from water. Thus, it is preferred that the composition of the present invention be a non-aqueous composition.

Oil ingredients which may be used in the present invention include solid oils, semi-solid oils and liquid oils, and they may be used in a mixture of two or more. Examples of the solid or semi-solid oils include Japan wax, hydrogenated beef tallow, carnauba wax, candelilla wax, rice wax, beeswax, ceresine wax, microcrystalline wax, paraffin wax, polyethylene wax, hydrogenated jojoba oil, lanolin, and vaseline. The amount of the oil used may be varied depending on the end use of the cosmetic composition, and is in the range from 1 to 90% by weight, preferably from 5 to 70% by weight.

Examples of liquid oils which may be used in the composition of the present invention include hydrocarbons such as liquid paraffin, liquid isoparaffin (liquid polyisobutylene) and squalene; animal or vegetable oils of natural origin such as olive oil and jojoba oil; silicone oils such as dimethylpolysiloxane; and synthetic esters such as isopropylmyristate. The amount of the liquid oil ingredient used depends also on the end use desired, and ranges from 1 to 90%., preferably from 5 to 70% by weight based on the total weight of the composition.

Pigments which may be used in the present invention include conventional cosmetic pigments. Examples of the pigments include body pigments such as talc, sericite, mica, kaolin, silica, nylon powder, polyethylene powder and cellulose powder; coloring agents such as carbon black, titanium oxide, iron oxide, zinc oxide, ultramarine, prussian blue, chromium oxide, dyestuffs of the organic tar series and lakes; complex pigments such as titanated oxide and iron oxide-coated mica. The particle surface of these pigments may be optionally treated with silicones, higher fatty acids, higher alcohols, aliphatic esters, metallic soaps, amino acids or alkylphosphates. It is preferred that one or more of these pigments be contained in the solid cosmetic compositions of the present invention in an amount from 0.1 to 95%, preferably from 5 to 70% by weight based on the total weight of the composition.

The oil-based solid cosmetic composition according to the present invention may optionally contain ingredients other than those described above as long as they do hot detrimentally affect the properties of the composition. These optional ingredients include other conventional cosmetically acceptable substances, such as surfactants, pharmaceutically acceptable ingredients, preservatives, antioxidants, moisturizers, UV absorbers and perfumes.

The oil-based solid cosmetic composition of the present invention may be prepared by any conventional process, such as by heating, blending or stirring the above described ingredients to form make-up cosmetics such as lipsticks, foundations, eye shadows and eye liners.

The polyether modified silicones used in the oil-based solid cosmetic composition of the present invention have a specific chemical structure, and are in a liquid state when water is not present. However, quite surprisingly, the viscosity of the polyether modified silicone rapidly increases when a small amount of water (1 to 20% by weight) is added, and further addition of water eventually causes the polyether modified silicone to acquire a gel state. At this point, no more water can be absorbed.

While not wanting to be bound by the mechanism of action of the present invention, the inventors believe that these phenomena help explain the effects of the invention as follows: When the composition is applied to the skin, it can be smoothly extended on the surface of the skin because the viscosity of the composition as manufactured is low. Pigments contained in the composition can therefore be distributed thinly and uniformly over the skin. This provides excellent feel during use and beautiful make-up appearance. After the composition is applied, the polyether modified silicone in the film formed on the skin surface becomes viscous, due to the supply of moisture from the skin or breath of the wearer. This increase in viscosity helps to hold the pigments more securely, thus providing prolonged beautiful appearance.

Having generally described this invention, a further understanding can be obtained by reference to certain specific examples which are provided herein for purposes of illustration only and are not intended to be limiting unless otherwise specified.

EXAMPLES

Example 1: Lipstick

The ingredients, as shown in Table 1, were heated at 80° C., uniformly blended, cast in a mould, and cooled down to prepare lipsticks.

A panel consisting of 10 members used the lipsticks and evaluated them according to the following criteria:

A: Eight members or more out of ten evaluated as good.
B: Six to seven members out of ten evaluated as good.

C: Four to five members out of ten evaluated as good.
D: Three or less members out of ten evaluated as good.

TABLE 1

| Formulation | Invention Composition | Comparative Compositions | | |
|---|---|---|---|---|
| (Parts by weight) | L-1 | L-2 | L-3 | L-4 |
| Ceresine | 10 | 10 | 10 | 10 |
| Paraffin wax | 8 | 8 | 8 | 8 |
| Candelilla wax | 2 | 2 | 2 | 2 |
| Squalane | 25 | 25 | 25 | 25 |
| Castor oil | 37 | 37 | 37 | 37 |
| Liquid paraffin | 0 | 10 | 0 | 5 |
| Polyisobutylene | 0 | 0 | 10 | 5 |
| Polyether modified silicone (Formula (1) where $R^1$ to $R^9 = CH_3$, $R^{1'} = H$, m = 50 to 100, n = 1 to 5, x = 7 to 15, y = 0, p = 3; polyoxyethylene: 17%, $\overline{MW}$ = 8000) | 10 | 0 | 0 | 0 |
| Titanium oxide | 2 | 2 | 2 | 2 |
| Pigment (D&C Red No. 6, CI 15850) | 2 | 2 | 2 | 2 |
| Pigment (D&C Red No. 7 Ca Lake, CI 15850) | 1 | 1 | 1 | 1 |
| Pigment (FD&C Yellow No. 5 Al Lake, CI 19140) | 3 | 3 | 3 | 3 |
| Antioxidant | Suitable amount | | | |
| Perfume | Suitable amount | | | |

TABLE 2

| Items | Invention Product | Comparative Products | | |
|---|---|---|---|---|
| | L-1 | L-2 | L-3 | L-4 |
| Appearance after application | A | B | B | B |
| Leave mark on cups | B | D | D | D |
| Color staying power on lips | A | D | C | D |
| Difficult in oozing | A | C | B | B |

As Table 2 shows, the lipstick according to the present invention provides excellent make-up appearance, and excellent ratings in the other evaluation areas.

Example 2 Oil-based Foundation

The waxes and oil ingredients, listed in Table 3, were dissolved at 90° C., to which the pigments and perfume of Table 3 were mixed. The obtained mixture was cast in a metal mould, cooled down and charged into a container to prepare an oil-based foundation composition.

Similar evaluations as described in Example 1 were performed. The results are shown in Table 4.

TABLE 3

| Formulation | Invention Composition | Comparative Composition | |
|---|---|---|---|
| (Parts by weight) | F-1 | F-2 | L-3 |
| Mica (hydrophobia treatment*) | 50 | 50 | 50 |
| Titanated mica (hydrophobic treatment*) | 9 | 9 | 9 |

TABLE 3-continued

| Formulation | Invention Composition | Comparative Composition | |
|---|---|---|---|
| (Parts by weight) | F-1 | F-2 | L-3 |
| Iron oxide (hydrophobic treatment*) | 1 | 1 | 1 |
| Ultramarine (hydrophobic treatment*) | 2 | 2 | 2 |
| Liquid paraffin | 0 | 15 | 0 |
| Diisostearyl malate | 0 | 0 | 15 |
| Polyether modified silicone (Formula (1) where $R^1$ to $R^9 = CH_3$, $R^{1'} = H$, m = 50 to 100, n = 1 to 5, x = 7 to 15, y = 0, p = 3, polyoxyethylene: 17%, $\overline{MW}$ = 8000) | 15 | 0 | 0 |
| Paraffin wax | 5 | 5 | 5 |
| Branched aliphatic cholesteryl ester | 7 | 7 | 7 |
| Squalane | 11 | 11 | 11 |
| Antioxidant | Suitable amount | | |
| Perfume | Suitable amount | | |

*) Hydrophobic treatment = silicone treatment

TABLE 4

| Evaluation | Invention Product | Comparative Products | |
|---|---|---|---|
| Item | F-1 | F-2 | F-3 |
| Long lasting effect | B | C | D |

As Table 4 shows, the oil-based foundation according to the present invention is clearly superior to the comparative products F-2 and F-3 with respect to prolonged retention of the appearance of the make-up.

Example 3 Powder Cake Eye Shadow

The powder ingredients listed in Table 5 were mixed with a blender, into which a heated, melted mixture of the oil ingredients in Table 5 was sprayed. The resulting mixture was further blended. The resulting material was crushed, and compression-molded with a molding machine to obtain powder cake eye shadows.

Similar evaluation as described in Example 1 were performed. The results are shown in Table 6.

TABLE 5

| Formulation | Invention Product | Comparative Products | |
|---|---|---|---|
| (Parts by weight) | I-1 | I-2 | I-3 |
| Talc (hydrophobic treatment*) | 15 | 15 | 15 |
| Sericite (hydrophobic treatment*) | 30 | 30 | 30 |
| Titanated mica (hydrophobic treatment*) | 35 | 35 | 35 |
| Ultramarine (hydrophobic treatment*) | 5 | 5 | 5 |
| Iron oxide (hydrophobic treatment*) | 2 | 2 | 2 |
| Polyether modified silicone (Formula (2) where $R^{10}$ to $R^{14} = CH_3$, | 10 | — | — |

TABLE 5-continued

| Formulation | Invention Product | Comparative Products | |
|---|---|---|---|
| (Parts by weight) | I-1 | I-2 | I-3 |
| $R^{2'}$ to $R^{4'}$ = H, m1 = 50 to 100, n1 = 1 to 5, x1 = 7 to 15, y1 = 0, p1 = 3, polyoxyethylene: 34%, MW = 10000) | | | |
| Diisostearyl malate | — | 10 | — |
| Castor oil | — | — | 10 |
| Liquid paraffin | 2 | 2 | 2 |
| Paraffin | 1 | 1 | 1 |

*) Hydrophobic treatment = silicone treatment

TABLE 6

| Evaluation Item | Invention Product I-1 | Comparative Products | |
|---|---|---|---|
| | | I-2 | I-3 |
| Long lasting effect | B | C | D |

Example 4

The general procedure of Example 1 was followed to prepare a lipstick, except that a polyether modified silicone of Formula (2) where $R^{10}$ to $R^{14}$=$CH_3$, $R^{2'}$ to $R^{4'}$=H, m1=50 to 100, n1=1 to 5, x1=7 to 15, y1=1, p1=3, with the content of polyoxyethylene being 34% (based on the weight of the polyether modified silicone) and having an average molecular weight of 10,000, was used instead of the polyether modified silicone employed in the invention product L-1.

Example 5

The general procedure of Example 1 was followed to prepare a lipstick, except that a polyether modified silicone of Formula (1) where $R^1$ to $R^9$=$CH_3$, $R^{1'}$=H, m=60 to 90, n=3 to 8, x=5 to 10, y=0, p=3, with the content of polyoxyethylene being 11% (based on the weight of the polyether modified silicone) and having an average molecular weight of 8,000, was used instead of the polyether modified silicone employed in the invention product L-1.

Example 6

The general procedure of Example 1 was followed to prepare a lipstick, except that a polyether modified silicone of Formula (1) where $R^1$ to $R^9$=$CH_3$, $R^{1'}$=H, m=20 to 70, n=1 to 5, x=7 to 15, y=0, p=3, with the content of polyoxyethylene being 26% (based on the weight of the polyether modified silicone) and having an average molecular weight of 6,300, was used instead of the polyether modified silicone employed in the invention product L-1.

Example 7

The general procedure of Example 1 was followed to prepare a lipstick, except that a polyether modified silicone of Formula (1) where $R^1$ to $R^9$=$CH_3$, $R^{1'}$=H, m=100 to 150, n=1 to 5, x=7 to 15, y=O, p=3, with the content of polyoxyethylene being 13% (based on the weight of the polyether modified silicone) and having an average molecular weight of 12,500, was used instead of the polyether modified silicone employed in the invention product L-1.

The lipsticks prepared in Examples 4 to 7 all provided excellent feel during use, and maintained beautiful make-up appearance for a prolonged period of time.

Example 8

The general procedure of Example 2 was followed to prepare an oil-based foundation, except that a polyether modified silicone of Formula (2) where $R^{10}$ to $R^{14}$=$CH_3$, $R^{2'}$ to $R^{4'}$=H, m1=50 to 100, n1=0, x1=7 to 15, y1=1, p1=3, with the content of polyoxyethylene being 34% (based on the weight of the polyether modified silicone) and having an average molecular weight of 10,000, was used instead of the polyether Modified silicone employed in the invention product F-1.

Example 9

The general procedure of Example 2 was followed to prepare an oil-based foundation, except that a polyether modified silicone of Formula (1) where $R^1$ to $R^9$=$CH_3$, $R^{1'}$=H, m=60 to 90, n=3 to 8, x=5 to 100, y=0, p=3, with the content of polyoxyethylene being 11% (based on the weight of the polyether modified silicone) and having an average molecular weight of 8,000, was used instead of the polyether modified silicone employed in the invention product F-1.

Example 10

The general procedure of Example 2 was followed to prepare an oil-based foundation, except that a polyether modified silicone of Formula (1) where $R^1$ to $R^9$=$CH_3$, $R^{1'}$=H, m=50 to 100, n=1 to 5, x=5 to 10, y=15 to 23, p=3, with the content of polyoxyethylene being 25% (based on the weight of the polyether modified silicone) and having an average molecular weight of 11,000, was used instead of the polyether modified silicone employed in the invention product F-1.

The oil-base foundations prepared in Examples 8 to 10 all provided excellent feel during use, and maintained beautiful make-up appearance for a prolonged period of time.

Example 11

The general procedure of Example 3 was followed to prepare a powder eye shadow, except that a polyether modified silicone of Formula (1) where $R^1$ to $R^9$=$CH_3$, $R^{1'}$=H, m=50 to 100, n=1 to 5, x=5 to 15, y=7 to 15, p=3, with the content of polyoxyethylene being 17% (based on the weight of the polyether modified silicone) and having an average molecular weight of 8,000, was used instead of the polyether modified silicone employed in the invention product I-1. This powder eye shadow gave excellent feel during use, and maintained beautiful make-up appearance for a prolonged period of time.

Obviously, numerous modifications and variations of the present invention are possible in light of the above teachings. It is therefore to be understood that within the scope of the appended claims, the invention may be practiced otherwise than as specifically described herein.

What is claimed is:

1. An oil-based solid cosmetic composition consisting essentially of:

(A) one or more polyoxyalkylene modified organopolysiloxanes represented by one of the following formulas (1) to (4):

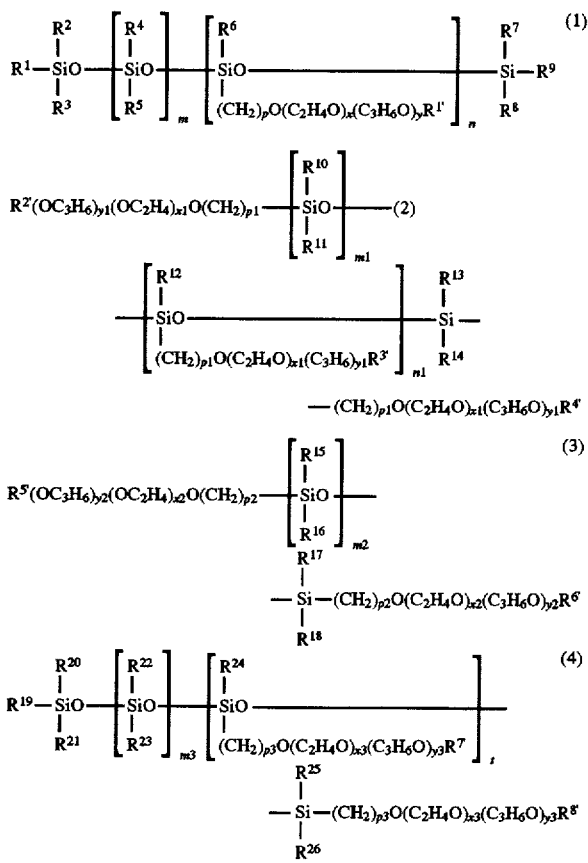

wherein $R^1$ to $R^{26}$ are the same or different from each other, and independently represent $C_1$ to $C_{32}$ linear or branched alkyl, a hydrogen atom or a phenyl group; $R^{1'}$ to $R^{5'}$ are the same or different from each other, and independently represent a $C_1$ to $C_{32}$ linear or branched alkyl group or a hydrogen atom; p, p1, p2 and p3 independently denote a number from 1 to 18; and x, x1, x2, x3, y, y1, y2, y3, m, m1, m2, m3, n, n1 and t are average numbers which make the proportion of the polyoxyalkylene group contained in the molecule from 1 to 50% by weight;

(B) one or more cosmetically acceptable oils;

(C) one or more cosmetically acceptable pigments, wherein said composition comprises<1 wt.% water wherein said cosmetic is lipstick.

2. The oil-based solid cosmetic composition according to claim 1, wherein the parameters in formulas (1) to (4) are defined as follows:

$R^1$ to $R^{26}$: $C_1$ to $C_{25}$ linear or branched alkyl, wherein a portion of the groups are optionally a hydrogen atom.

$R^{1'}$ to $R^{8'}$: Hydrogen atom or $C_1$ to $C_{18}$ linear or branched alkyl, p to p3: 1 to 20, x to x3: 1 to 50, y to y3: 0 to 50, m to m3: 1 to 500, n to n1: 1 to 100, and t: 1 to 100.

3. The oil-based solid cosmetic composition according to claim 1, wherein the parameters in formulas (1) to (4) are defined as follows:

$R^1$ to $R^{26}$: $C_1$ to $C_{22}$ linear or branched alkyl, wherein a portion of the groups are optionally a hydrogen atom.

$R^{1'}$ to $R^{8'}$: Hydrogen atom, p to p3: 1 to 5, x to x3: 1 to 50, y to y3: 0 to 20, m to m3: 10 to 300, n to n1: 1 to 50, and t: 1 to 50.

4. The composition according to claim 1, wherein the proportions of ingredients (A) to (C) are defined as follows:

(A): 5 to 30% by weight, (B): 5 to 70% by weight, (C): 5 to 70% by weight, based on the total weight of the composition.

5. The composition of claim 1, wherein the portion of ingredients (A)–(C) is as follows:

A) 0.5 to 50 wt.%;

B) 1 to 90 wt.%; and

C) 0.1 to 95 wt.%, based on the total weight of the composition.

6. The oil-based solid cosmetic composition of claim 1, wherein said composition is free from water.

7. The oil-based solid cosmetic composition of claim 1, wherein said composition is substantially free from water.

8. The oil-based solid cosmetic composition of claim 1, wherein said polyoxyalkylene modified organopolysiloxane is of formula (1).

9. The oil-based solid cosmetic composition of claim 1, wherein $R^1$ to $R^9$ are each $CH_3$, $R^{1'}$ is H, m is 50 to 100, n is 1 to 5, x is 7 to 15, y is 0 and p is 3 in said polyoxyalkylene modified organopolysiloxane of formula (1).

10. The oil-based solid cosmetic composition of claim 1, wherein said cosmetically acceptable oil is selected from the group consisting of Japan wax, halogenated beef tallow, carnauba wax, candelilla wax, rice wax, beeswax, ceresine wax, microcrystalline wax, paraffin wax, polyethylene wax, hydrogenated jojoba oil, lanolin, vaseline, liquid paraffin, liquid isoparaffin, squaline, olive oil, jojoba oil, dimethylpolysiloxane, isopropylmyristate and a mixture thereof.

11. The oil-based solid cosmetic composition of claim 1, wherein said cosmetically acceptable oil comprises a mixture of two or more of:

i) a solid oil;

ii) a semi-solid oil; and iii) a liquid oil.

12. The oil-based solid cosmetic composition of claim 1, wherein the proportion of the polyoxyalkylene group contained in the molecule is from 5 to 40% by weight.

* * * * *